(12) United States Patent
Pinsonneault

(10) Patent No.: US 8,639,523 B1
(45) Date of Patent: Jan. 28, 2014

(54) SYSTEMS AND METHODS FOR MANAGING A PRESCRIPTION REWARDS PROGRAM

(75) Inventor: Roger Pinsonneault, Alpharetta, GA (US)

(73) Assignee: McKesson Financial Holdings (BM)

(*) Notice: Subject to any disclaimer, the term of this patent is extended or adjusted under 35 U.S.C. 154(b) by 418 days.

(21) Appl. No.: 12/420,288

(22) Filed: Apr. 8, 2009

Related U.S. Application Data

(60) Provisional application No. 61/080,265, filed on Jul. 13, 2008.

(51) Int. Cl.
- *G06Q 10/00* (2012.01)
- *G06Q 50/00* (2012.01)
- *G06Q 30/00* (2012.01)
- *G06Q 40/00* (2012.01)

(52) U.S. Cl.
USPC .................. 705/2; 705/3; 705/4; 705/14.36

(58) Field of Classification Search
USPC .................................................. 705/2–4, 14
See application file for complete search history.

(56) References Cited

U.S. PATENT DOCUMENTS

| | | | |
|---|---|---|---|
| 5,628,530 | A | 5/1997 | Thornton |
| 6,012,035 | A | 1/2000 | Freeman et al. |
| 6,757,898 | B1 | 6/2004 | Ilsen et al. |
| 6,769,228 | B1 | 8/2004 | Mahar |
| 7,155,397 | B2 | 12/2006 | Alexander et al. |
| 7,578,430 | B2 * | 8/2009 | Michelsen et al. ............ 235/375 |
| 2002/0002495 | A1 * | 1/2002 | Ullman ........................... 705/21 |
| 2002/0087583 | A1 | 7/2002 | Morgan et al. |
| 2002/0111832 | A1 | 8/2002 | Judge |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0149625 | A1 | 8/2003 | Leonardi et al. |

(Continued)

FOREIGN PATENT DOCUMENTS

| | | |
|---|---|---|
| CA | 2482370 A1 | 3/2006 |
| WO | WO 9503569 A3 | 2/1995 |
| WO | WO 0039737 A1 | 7/2000 |
| WO | WO 2007025295 A2 | 3/2007 |

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Joseph Burgess
(74) *Attorney, Agent, or Firm* — Sutherland Asbill & Brennan LLP

(57) ABSTRACT

Systems and methods for managing a prescription rewards program include receiving, at a switch, an adjudicated prescription claim transaction, where the adjudicated prescription claim transaction includes an indication that the prescription claim transaction has been approved by a claim processor. The systems and methods further include identifying, from the adjudicated prescription claim transaction, a patient associated with the adjudicated prescription claim transaction, retrieving, from a database associated with the switch, a reward accumulator value associated with the patient, and updating the reward accumulator value associated with the patient based at least in part on the adjudicated prescription claim transaction. The systems and methods may further include determining that a threshold value has been satisfied by the reward accumulator value, and issuing a reward message based at least in part on the reward accumulator satisfying the threshold value.

18 Claims, 5 Drawing Sheets

(56) References Cited

U.S. PATENT DOCUMENTS

| | | |
|---|---|---|
| 2003/0154163 A1 | 8/2003 | Phillips et al. |
| 2003/0200687 A1* | 10/2003 | Wolfe .............................. 40/634 |
| 2003/0229540 A1 | 12/2003 | Algiene |
| 2004/0039599 A1 | 2/2004 | Fralic |
| 2004/0073457 A1 | 4/2004 | Kalies |
| 2004/0078234 A1 | 4/2004 | Tallal, Jr. |
| 2004/0117323 A1 | 6/2004 | Mindala |
| 2004/0122736 A1* | 6/2004 | Strock et al. .................... 705/14 |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0149784 A1 | 7/2006 | Tholl et al. |
| 2006/0184391 A1 | 8/2006 | Barre et al. |
| 2006/0190323 A1* | 8/2006 | Olson et al. ..................... 705/14 |
| 2006/0259363 A1 | 11/2006 | Jhetam et al. |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |

OTHER PUBLICATIONS

Anonymous, ACS to Demonstrate Electronic Health Record Solution Suite at MMIS 2007 Conference; EHR Tools Consolidate Data Provide Useful Information at the Point of Care for Medicaid Providers, Payers, and Patients, PR Newswire, Aug. 13, 2007, Nev York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30. 2001, p. 1, New York, NY, USA.

Anonymous, Medic; On-Line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Non-final Office Action for U.S. Appl. No. 12/494,708 mailed Sep. 1, 2011.

Final Office Action for U.S. Appl. No. 12/494,718 mailed Aug. 2, 2012.

* cited by examiner

1

SYSTEMS AND METHODS FOR MANAGING A PRESCRIPTION REWARDS PROGRAM

CROSS REFERENCE TO RELATED APPLICATION

This application claims the benefit of priority to U.S. Provisional Application No. 61/080,265, filed Jul. 13, 2008, which is hereby incorporated by reference as if set forth fully herein.

FIELD OF THE INVENTION

Embodiments of the invention relate generally to prescription claim and prescription claim reversal transactions, and more particularly to systems and methods for managing a prescription rewards program.

BACKGROUND OF THE INVENTION

Many pharmacy providers and/or their sponsors or affiliates offer a variety of incentives for customers to have their prescriptions filled at a specific pharmacy or one of a chain of pharmacies. To formally enroll in an incentive program the customer may have provided identifying information to the pharmacy in exchange for a customer identifier such as a token, card, sticker, ID number, etc. When the token is presented by the enrolled customer at a participating pharmacy during the pick-up and/or purchase of prescription medication, the enrolled customer may be entitled to an incentive (e.g., copay discount, coupon, free prescription refill, etc.). For example, a pharmacy at a department and/or grocery store may provide such incentives to those customers who have obtained a credit card associated with the department or grocery store. Alternatively, a grocery store may provide a token (e.g., a bar code) that may be presented at checkout to apply special discounts to particular items purchased at the store.

However, current rewards programs involving prescription drug purchase and/or fulfillment are limited in their effectiveness. For instance, rewards programs for prescription drug purchases and/or fulfillments may be inconvenient, ineffective, and/or prohibitively expensive in their administration. For instance, the type and frequency of rewards offered may be limited due to lack of the ability to efficiently track a customer's participation in the rewards program from various transactions made from various locations. Current rewards programs may also be inconvenient for customer in that many such programs require a token or other identifier to be presented by a customer during a transaction otherwise the reward may not be awarded or the transaction may not be tracked for future rewards. A need exists in the art for systems, methods, and apparatus for addressing some or all of the shortcomings and limitations of existing rewards programs for transactions involving prescription drug purchases and/or fulfillments.

BRIEF DESCRIPTION OF THE INVENTION

According to an embodiment of the invention, there is disclosed a method for managing a prescription rewards program that includes receiving, at a switch, an adjudicated prescription claim transaction, where the adjudicated prescription claim transaction includes an indication that the prescription claim transaction has been approved by a claim processor. The method further includes identifying, from the adjudicated prescription claim transaction, a patient associated with the adjudicated prescription claim transaction, retrieving, from a database associated with the switch, a reward accumulator value associated with the patient, and updating the reward accumulator value associated with the patient based at least in part on the adjudicated prescription claim transaction.

In accordance with one aspect of the invention, the method further includes determining that a threshold value has been satisfied by the reward accumulator value, and issuing a reward message based at least in part on the reward accumulator satisfying the threshold value. According to another aspect of the invention, issuing a reward message may include issuing a reward message that indicates a discount associated with the payment of a prescription. In accordance with yet another aspect of the invention, the method further includes determining that the prescription associated with the prescription claim transaction is eligible for rewards processing prior to retrieving a reward accumulator value associated with the patient. According to another aspect of the invention, the method further includes receiving an approved prescription claim reversal transaction, and decrementing the reward accumulator value based at least in part on the approved prescription claim reversal transaction. In accordance with yet another aspect of the invention, updating the reward accumulator value associated with the patient includes incrementing the reward accumulator value based at least in part on the adjudicated prescription claim.

According to another aspect of the invention, the method further includes, prior to receiving an adjudicated prescription claim transaction, receiving a prescription claim transaction, identifying the patient from the prescription claim transaction, and creating the reward accumulator associated with the patient. In accordance with yet another aspect of the invention, identifying a patient associated with the adjudicated prescription claim includes parsing the adjudicated prescription claim transaction to identify patient related data, and matching the patient related data with a database entry. According to another aspect of the invention, parsing the adjudicated prescription claim transaction to identify patient related data includes parsing the adjudicated prescription claim transaction to identify at least one of a pharmacy identifier, patient name, patient address, patient date of birth, or patient gender code. In accordance with yet another aspect of the invention, the method further includes, prior to retrieving the reward accumulator value associated with the patient, enrolling the patient associated with the adjudicated prescription claim transaction in a prescription rewards program, where the enrollment includes associating the patient with the reward accumulator value.

In accordance with another embodiment of the invention, there is disclosed a system for managing a prescription rewards program that includes a memory device, where the memory device stores a plurality of reward accumulator values, and where each accumulator value is associated with a patient. The system further includes a processor in communication with the memory device, where the processor is configured to execute computer-executable instructions to receive an adjudicated prescription claim transaction, where the adjudicated prescription claim transaction includes an indication that the prescription claim transaction has been approved by a claim processor. The processor executes additional computer-executable instructions to identify, from the adjudicated prescription claim transaction, a patient associated with the adjudicated prescription claim transaction, retrieve, from the memory device, a reward accumulator value associated with the patient, and update the reward accumulator value associated with the patient based at least in part on the adjudicated prescription claim transaction.

According to one aspect of the invention, the processor is further configured to execute instructions to determine that a threshold value has been satisfied by the reward accumulator value and issue a reward message based at least in part on the reward accumulator satisfying the threshold value. In accordance with another aspect of the invention, the computer-executable instructions to issue a reward message include issuing a reward message that indicates a discount associated with the payment of a prescription. According to yet another aspect of the invention, the processor is further configured to execute instructions to determine that the prescription associated with the prescription claim transaction is eligible for rewards processing prior to retrieving a reward accumulator value associated with the patient. In accordance with another aspect of the invention, the processor is further configured to execute instructions to receive an approved prescription claim reversal transaction and decrement the reward accumulator value based at least in part on the approved prescription claim reversal transaction. According to yet another aspect of the invention, the computer-executable instructions to update the reward accumulator value associated with the patient include incrementing the reward accumulator value based at least in part on the adjudicated prescription claim.

In accordance with another aspect of the invention, the processor is further configured to execute instructions to, prior to receiving an adjudicated prescription claim transaction, receive a prescription claim transaction, identify the patient from the prescription claim transaction, and create the reward accumulator associated with the patient. According to yet another aspect of the invention, the computer-executable instructions to identify a patient associated with the adjudicated claim include parsing the adjudicated prescription claim transaction to identify patient related data and matching the patient related data with one of a plurality of database entries. In accordance with another aspect of the invention, the software instructions to parse the adjudicated prescription claim transaction to identify patient related data include parsing the adjudicated prescription claim transaction to identify at least one of a pharmacy identifier, patient name, patient address, patient date of birth, or patient gender code. According to yet another aspect of the invention, the processor is further configured to execute computer-executable instructions to, prior to retrieving the reward accumulator value associated with the patient, enroll the patient associated with the adjudicated prescription claim transaction in a prescription rewards program, where the enrollment includes associating the patient with the reward accumulator value.

DETAILED DESCRIPTION OF EMBODIMENTS OF THE INVENTION

Figure 1:
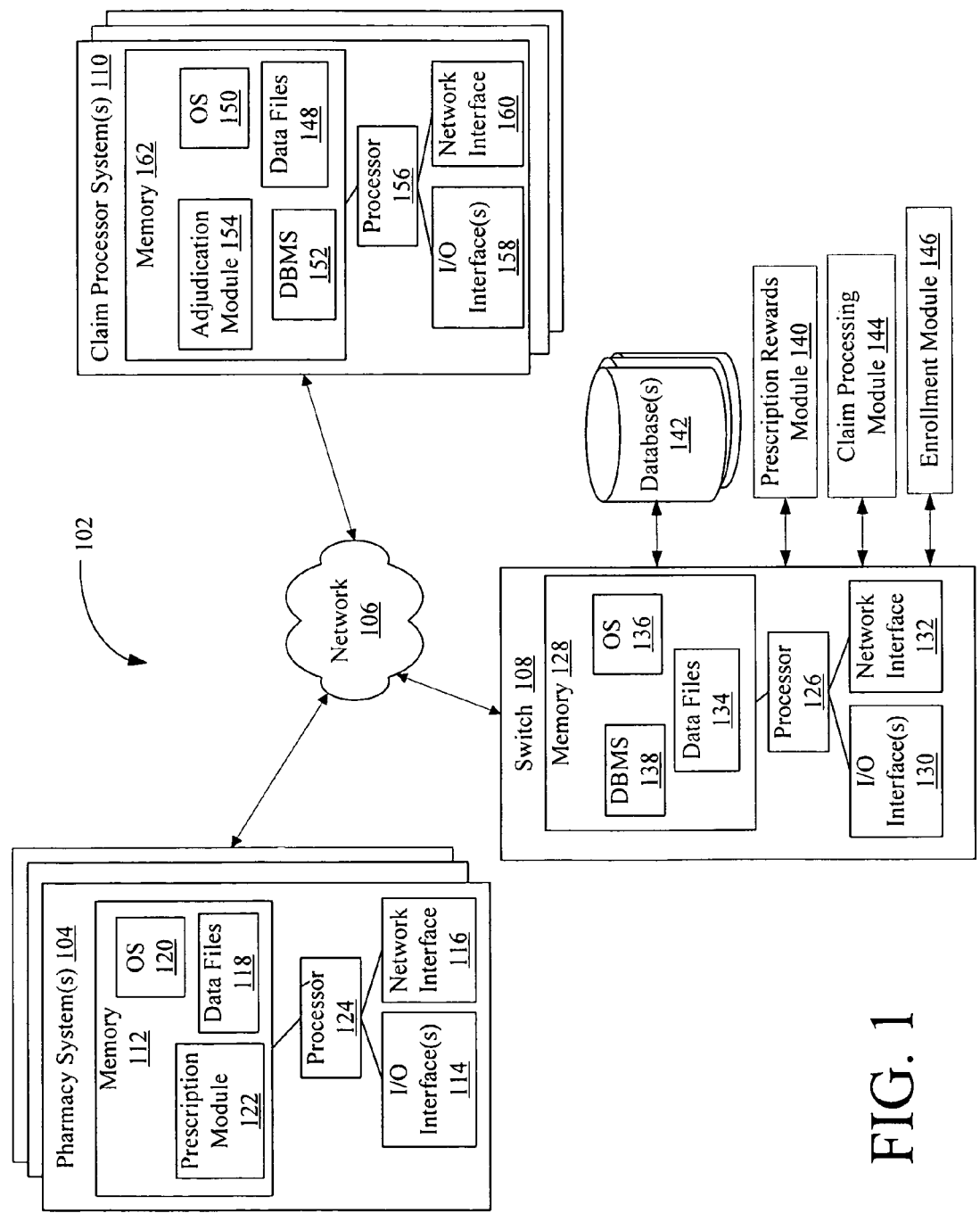
FIG. 1 shows an example system for managing a prescription rewards program in accordance with an example embodiment of the invention.

Embodiments of the invention are directed to a centralized switch (or clearinghouse) or other processing entity that processes and/or routes prescription claim and/or prescription claim reversal transactions that are submitted by a pharmacy to be adjudicated by a particular claim processor (e.g., health insurance provider, government program, third party payer system, etc.), and as part of that processing, the switch tracks patient usage of a particular pharmacy (or pharmacies) to offer various rewards, incentives, discounts, or the like to the patient whose prescription is being filled by that pharmacy. In an example embodiment of the invention, the switch manages the prescription rewards program for individual pharmacy customers.

In an example embodiment of the invention, data cleansing and/or matching processes are applied to pharmacy, patient, physician, and claim information submitted in a prescription claim and/or prescription claim reversal transaction for adjudication, and a cross-index for all patients associated with a particular pharmacy (or pharmacy sponsor such as a chain, department store, grocery store, etc.) is created and maintained in a database (e.g., a prescription rewards database).

For example, a matching process may be applied to potential patient identifying information including pharmacy, patient, physician, and claim information contained in a prescription claim (or reversal) transaction submitted for adjudication to identify the patient associated with the submitted claim (or reversal) transaction. The matching process weighs the strength of the matched patient identifying data contained in the prescription claim (or reversal) transaction and the patient identification data maintained in the database to determine if the patient associated with the submitted claim (or reversal) transaction corresponds to a patient entry in the database (e.g., a cross-index such as an Enterprise Master Patient Index (EMPI). Use of an EMPI may allow for the unique identification and/or confirmation of supplied identification information using data cleansing and/or matching processes to automatically locate patient information in a database or to create new entries in a database associated with a patient. In example embodiments of the invention, the EMPI may be used to identify whether or not a patient is enrolled in a prescription rewards program (or member patient's family, for instance, under the same healthcare insurance plan) using probabilistic matching techniques typically based on demographic information associated with the patient of the submitted transaction. For example, a transaction containing a patient's telephone number, date of birth, and zip code, may be used to determine that the patient associated with the submitted transaction is enrolled in a prescription rewards program and the patient's associated reward information should be updated and/or applied accordingly.

The information of the database entry associated with the patient is updated as a patient utilizes additional prescription transactions with a particular pharmacy, and as a result, rewards, incentives, discounts, or the like may be indicated by the updated information reaching and/or exceeding a threshold value or by another type of indicator. A reward message (or reward indicator) may then be sent to the pharmacy for a reward to be applied to the prescription transaction and/or a reward message (or reward indicator) may be sent to a third party system (such as the pharmacy sponsor) for reporting and/or analysis. In another embodiment of the invention, rather than the reward itself being sent to the pharmacy, a reward status indicator may be returned in the prescription claim response or prescription claim reversal response to the pharmacy to facilitate pharmacist and patient communications relative to the patient's current status in the rewards program.

The systems and methods described herein may provide several advantages including allowing for a centralized administration of the prescription rewards program, which minimizes the impact of providing such a prescription rewards system on pharmacists at a pharmacy, and allowing for external patient enrollment and/or prescription rewards tracking that can track rewards accumulation based on prescription claim transactions occurring at various pharmacy locations and may provide more flexibility in reward possibilities. In an example embodiment of the invention, the systems and methods described herein may be implemented concurrently with and/or in addition to credit card programs, merchant loyalty programs, and the like. Such functionality likely increases patient (or customer) loyalty and increases brand awareness. Moreover, the management of prescription transaction information for all patients utilizing the pharmacy allows for a variety of types of rewards, incentives, discounts, etc. to be offered to customers of the pharmacy. The terms "patient" and "customer" of the pharmacy are used synonymously throughout the descriptions of example embodiments of the invention below.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention are described below with reference to block diagrams and flowchart illustrations of systems, methods, apparatuses and computer program products. It will be understood that each block of the block diagrams and flowchart illustrations, and combinations of blocks in the block diagrams and flowchart illustrations, respectively, can be implemented manually and/or by computer program instructions. With respect to computer program instructions, they may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data-processing apparatus to cause a series of operational elements or steps to be performed on the computer or other programmable apparatus to produce a computer-implemented process such that the instructions that execute on the computer or other programmable apparatus provide elements or steps for implementing one or more functions specified in the flowchart block or blocks.

Accordingly, blocks of the block diagrams and flowchart illustrations may support combinations of means for performing the specified functions, combinations of elements or steps for performing the specified functions, and program instruction means for performing the specified functions. It will also be understood that each block of the block diagrams and flowchart illustrations, and combinations of blocks in the block diagrams and flowchart illustrations, can be implemented manually or by special purpose hardware-based computer systems that perform the specified functions, elements or steps, or combinations of special purpose hardware and computer instructions.

According to an example embodiment of the invention, there may be a system and method for managing a prescription rewards program such that the prescription rewards may be made available to a customer of the pharmacy without the need for the customer to obtain and present a particular rewards identifier via a rewards card, bar code, credit card, or the like. FIG. 1 shows an example prescription rewards system 102 for managing a prescription rewards program in accordance with an example embodiment of the invention. The overall prescription rewards system 102 of FIG. 1 may include one or more pharmacy systems 104 (e.g., a pharmacy point of service device), a switch 108, and one or more claim processor systems 110 (e.g., insurance programs, government funded programs, benefits managers, drug manufacturers, other vendors and/or business associates of healthcare service providers, government and/or non-government entities providing financial and/or administrative services, and the like).

Each pharmacy system 104, switch 108, and/or claim processor system 110 may be configured for accessing and reading associated computer-readable media having stored thereon data and/or computer-executable instructions for implementing the various methods in accordance with example embodiments of the invention. Generally, network devices and systems, including the one or more pharmacy systems 104, switch systems 108, and claim processor systems 110 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art.

The pharmacy system 104 may comprise any processor-driven device, such as a personal computer, laptop computer, handheld computer, and the like. The pharmacy system 104 may include any processor-driven device that is configured for receiving, processing, and fulfilling prescription transactions from patients and/or healthcare providers (physician offices, clinics, hospitals, or other prescribing entities) via the switch 108 or otherwise. In addition to having a processor 124, the pharmacy system 104 may further include a memory 112, input/output ("I/O") interface(s) 114 and a network interface 116. The memory 112 may store data files 118 and various program modules, such as an operating system ("OS") 120 and a prescription module 122. The prescription module 122 may receive, process, and respond to prescriptions received from healthcare providers via the switch 108 (or received in another manner) as well as generate claim transactions relating to the filled (or to be filled) prescription to be routed to the claim processor system 110 via the switch 108. The prescription module 122 may include a web browser or other software, including a dedicated program, for interacting with the switch 108 via a web portal accessible through the web browser or via other communication means. For example, a user such as a pharmacist, physician, or an agent thereof (e.g., nurse, assistant, office clerk, etc.) may utilize the prescription module 122 to communicate with the switch 108. The prescription module 122 may also communicate with the claim processor system 110 or other third party system(s).

Still referring to the pharmacy system 104, the I/O interface(s) 114 may facilitate communication between the processor 124 and various I/O devices, such as a keyboard, mouse, printer, microphone, speaker, monitor, bar code readers/scanners, radio frequency identification (RFID) readers, and the like. The network interface 116 may take any of a number of forms, such as a network interface card, a modem, a wireless network card, and the like. These and other components of the pharmacy system 104 will be apparent to those of ordinary skill in the art and are therefore not discussed in more detail herein.

The switch 108 may include any processor-driven device that is configured for receiving, processing, and fulfilling prescription drug related requests and/or prescription claim transactions for adjudication from the pharmacy system 104 and/or claim processor systems 110. The switch 108 may include a processor 126, a memory 128, input/output ("I/O") interface(s) 130, and a network interface 132. The memory 128 may store data files 134 and various program modules, such as an operating system ("OS") 136 and a database management system ("DBMS") 138. In an example embodiment of the invention, a prescription rewards module 140 of the switch 108 provides the web portal functionality accessible by the prescription module 122 of the pharmacy system 104. A claim processing module 144 of the switch 108 may receive, process, and respond to requests and claim responses received from the adjudication module 154 of one or more claim processor systems 110.

An enrollment module 146 of the switch 108 may direct prompts to be presented to patients accessible through the pharmacy system 104 to provide patients the option of enrolling in a prescription rewards program and may capture and/or process enrollment information (e.g., patient identification data) obtained from a submitted prescription claim transaction. The enrollment module 146 allows for a centralized administration of the prescription rewards program, which minimizes the impact of providing such a prescription rewards system on pharmacists operating the pharmacy system, and allows for external patient enrollment and/or prescription rewards tracking that can track rewards accumulation based on prescription claim transactions occurring at various pharmacy locations and may provide more flexibility in reward possibilities.

In an example embodiment of the invention the prescription rewards module 140, the claim processing module 144, and/or the enrollment module 146 may be incorporated into the switch 108. In an alternative embodiment of the invention, the prescription rewards module 140, the claim processing module 144, and/or the enrollment module 146 may be in communication with, but separate from, the switch 108. For instance, one or more of the prescription rewards module 140, the claim processing module 144, and/or the enrollment module 146 may be hosted by a third party provider. In one example embodiment of the invention, the prescription rewards module 140, the claim processing module 144, and the enrollment module 146 may also be in communication with each other either electronically, or in an alternative embodiment, data may be provided between the modules manually. In yet another embodiment of the invention, the prescription rewards module 140, the claim processing module 144, and/or the enrollment module 146 may be combined and/or considered one module capable of performing the functionality of all the modules described herein.

In an example embodiment of the invention, the prescription rewards module 140 receives and processes adjudicated prescription claims and/or prescription claim reversals from the claim processing module 144 (discussed below) to determine if a reward should be associated with the adjudicated prescription claim and/or prescription claim reversal. In an example embodiment of the invention, the prescription rewards module 140 may include a back-end analytic, editing, messaging, and/or reporting system for prescription claims that receives awards and can send various information associated with the prescription claims (or reversals) receiving (or not receiving) rewards to the pharmacy system 104 or a third party system (not shown in FIG. 1). In an example embodiment of the invention, the claim processing module 144 may include a back-end analytic, editing, messaging, and/or reporting system for processing claim transactions between pharmacies and claim processors. In an example embodiment of the invention, the enrollment module 146 may include a back-end analytic, editing, messaging, and/or reporting system for enrolling patients in a prescription rewards program. A more detailed discussion of the functionality of the prescription rewards module 140, the claim processing module 144, and the enrollment module 146 is included below in the discussion of FIGS. 2-5.

The switch 108 may comprise computer-executable instruction for implementing one or more methods described herein, including processing, editing, and/or routing prescription transactions, as well as receiving adjudicated prescription claim and/or prescription claim reversal transactions. The switch 108 may determine whether an award should be distributed to the patient. The switch 108 may likewise be operative to store prescription data, patient data, and/or a listing of drugs available for various rewards/incentives in database(s) 142, which may include a distinct database and/or a database shared with the pharmacy system 104, and/or the claim processor system 110. In an example embodiment of the invention, the database(s) 142 in communication with the switch 108 may include additional data to facilitate rewards processing including: patient rosters and/or various EMPI indexes, listings, tables, counters, etc. for managing particular rewards including coupons, discount values, and other forms of rewards. The database(s) 142 may also include details and restrictions on the application and/or use of the rewards, as well as include other data that may be useful in rewards processing for the adjudicated prescription claim and/or prescription claim reversal transactions.

It will be appreciated that variations of FIG. 1 may be available in accordance with other example embodiments. As shown by FIG. 1, the switch 108 may be comprised of two or more distinct switches that are in communication with each other. One switch may be operative with the pharmacy system 104 and the claim processor systems 110, while the other switch may be operative with other pharmacy systems and claim processors. However, one switch may have a data processing arrangement with the other switch. Under the data processing agreement, one switch may be permitted to utilize or offer services of the other switch, including modules 140, 144, and 146, and the database 142. Accordingly, the services of the one switch, including modules 140, 144, and 146, and the database 142, may be available via other switches.

In other embodiments, one or more of the prescription rewards and/or enrollment processing functions described herein, and/or any of the associated data, may be performed and/or maintained by other entities of the system, such as in a distributed system in which the pharmacy system 104 and/or the claim processor systems 110 are operable to perform some or all of the prescription rewards and/or enrollment processing. Other variations are possible in other embodiments, and should still be considered within the scope of that described herein.

The claim processor system 110 may include any processor-driven device that is configured for receiving, processing, and fulfilling requests relating to claim adjudication processing. According to an example embodiment of the invention, the claim processor system 110 may process prescription claims received from pharmacy systems 104 via the switch 108. The claim processor system 110 may include a processor 156, a memory 162, input/output ("I/O") interface(s) 158, and a network interface 160. The memory 162 may store data files 148 and various program modules, such as an operating system ("OS") 150, a database management system ("DBMS") 152, and an adjudication module 154. The adjudication module 154 may receive, process, and respond to prescription claims and/or prescription claim reversals received from the switch 108.

In FIG. 1, a pharmacy system 104, switch 108, and claim processor system 110 may be in communication with each other via one or more networks 106. The one or more networks 106 may include any telecommunication and/or data network, whether public, private, or a combination thereof, including a public switched telephone network (PSTN), a cellular network, a local area network, a wide area network, an intranet, an internet, the Internet, intermediate hand-held data transfer devices, and/or any combination thereof and may be wired and/or wireless. The one or more networks 106 may also allow for real-time, off-line, and/or batch transactions to be transmitted between or among the pharmacy system 104, the switch 108, and the claim processor system 110. Due to network connectivity, various methodologies as described herein may be practiced in the context of distributed computing environments.

Those of ordinary skill in the art will appreciate that the system 102 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

Figure 2:
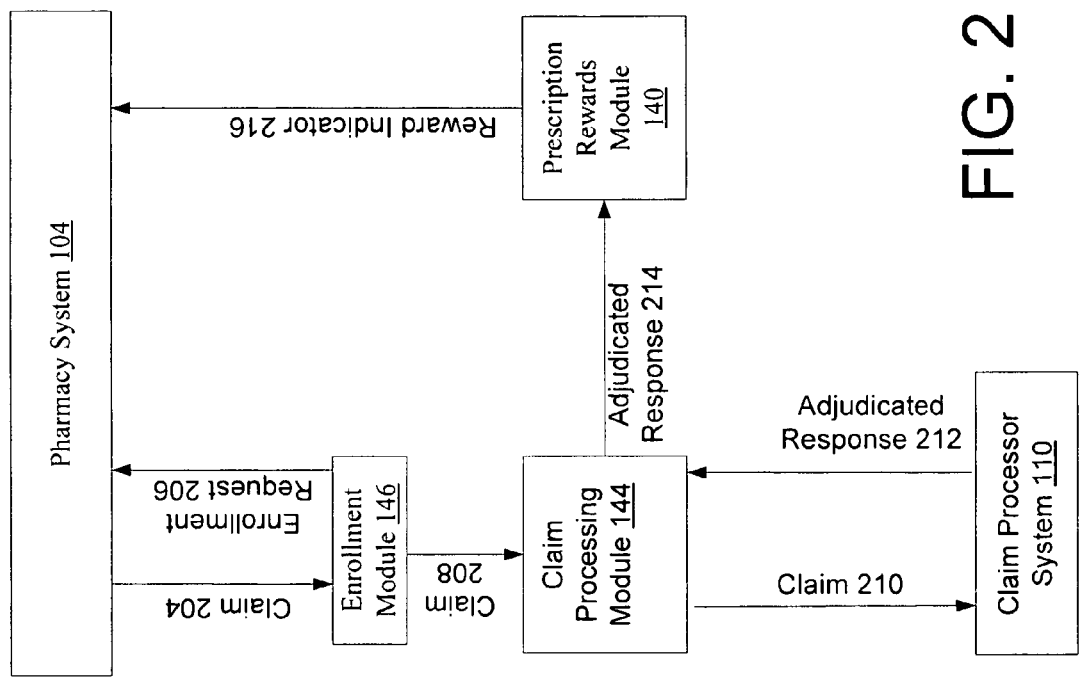
FIG. 2 shows an example block diagram for communications between the entities of a prescription rewards system for electronically submitting and processing prescription transactions in accordance with an example embodiment of the invention.

FIG. 2 shows an example block diagram 202 for communications between the entities of a prescription rewards system for electronically submitting and processing prescription transactions in accordance with an example embodiment of the invention. As shown in FIG. 2, once the pharmacy receives a prescription from the patient or directly from a healthcare provider's office, the pharmacy system 104 creates a claim (claim 204) to be adjudicated by the claim processor system 110. In the example data flow shown in FIG. 2, the prescription claim (or prescription claim reversal), claim 204, is sent from the pharmacy to an enrollment module 146. The claim 204 may be in accordance with a version of a National Council for Prescription Drug Programs (NCPDP) Telecommunication Standard, according to an example embodiment of the invention. For example, the claim 204 may include one or more of the following information:

Prescriber Information
  a. Name of the prescriber
  b. Prescriber identifier for a physician or healthcare provider Pharmacy Information
  a. Identifier of the pharmacy submitting the claim request
Patient Information
  a. Insurance or coverage information
  b. Name, address, date of birth
  c. Patient diagnosis/condition
Prescription Information
  a. Identification of the prescribed drug or product (e.g., National Drug Code (NDC))
  b. Prescription number
  c. Quantity and/or days supply of the prescribed drug or product
  d. Pricing information for the prescribed drug or product
  e. Date prescription written.

It will be also appreciated that while some example information has been illustrated for the example claim 204, alternate or additional information may also be included without departing from example embodiments of the invention. For example, the claim 204 may further include additional patient information such as a gender code for the patient. The claim 204 may also include a Banking Identification Number (BIN) and Processor Control Number (PCN) for identifying a claims processor system 110 as a destination of the claim 204.

The enrollment module 146 may extract patient identification data from the claim 204 to determine if the patient is enrolled in a prescription rewards program. If the patient is not enrolled, an enrollment request 206 may be sent back to the pharmacy system 104. In an example embodiment of the invention, the enrollment request 206 may be sent in the form of a denied prescription claim transaction requesting an indicator of whether or not a patient desires to enroll in a prescription rewards program. The claim may be resubmitted with an enrollment indicator indicating the patient's desire to enroll in a prescription rewards program (or indicate that the patient does not wish to enroll, or wishes to defer the decision to a later time).

In alternative embodiments of the invention, enrollment in the rewards program may be provided by a point of service enrollment located at the pharmacy, where the information is later uploaded or otherwise transmitted to the enrollment module to enroll a patient. In other embodiments of the invention a patient may enroll in the prescription rewards program through an interactive voice response (IVR) system, where the patient provides enrollment information and/or an enrollment acceptance indicator via selections and/or information provided through the IVR system. The IVR system may be connected to or otherwise in communication with the enrollment module 146 to provide the enrollment information to the enrollment module 146.

Next, as shown in FIG. 2, if the patient is already enrolled in a prescription rewards program, or once the enrollment process is complete, the claim 208 may be sent to the claim processing module 144 where the claim processing module 144 may simply route claim 208 to the corresponding claim processor system 110, or the claim processing module 144 may perform a variety of edits and/or analysis to ensure that claim 208 is in proper format for the corresponding claim processor system 110 or edit the claim to contain the appropriate information for proper adjudication. Once the edits (if any) provided by the claim processing module 144 on claim 208 are completed, the claim (claim 210) is routed to the appropriate claim processor system 110.

Once claim 210 is received by the claim processor system 110, the claim processor system 110 adjudicates the claim (or reversal) and indicates the results of the adjudication (e.g., approved or unapproved) in an adjudicated response (adjudicated response 212) that is routed back to the pharmacy system 104 through the claim processing module 144. The claim processing module 144 may review the adjudicated response 212 to update files pertaining to the transaction (e.g., patient eligibility files, transaction records, etc.). The update to the files may include sending information to the prescription rewards module 140 for updating. In an example embodiment of the invention, the prescription rewards module 140 may be in communication with the claim processing module 144 to obtain information for use in rewards processing and/or the administration of the prescription rewards program. In the example embodiment of FIG. 2, the prescription rewards module 140, enrollment module 146, and/or claim processing module 144 may be incorporated into the switch. In alternative embodiments of the invention, the prescription rewards module 140, enrollment module 146, and/or claim processing module 144 may be separate and distinct from the switch and in communication with the switch. In one example embodiment of the invention, the prescription rewards module 140 and the claim processing module 144 may be in communication with each other either electronically, or in an alternative embodiment, data may be provided between the two modules manually. The claim processing module 144 may also review and edit the adjudicated response 212 prior to forwarding the adjudicated response 212 to the prescription rewards module 140 as adjudicated response 214.

Next, the prescription rewards module 140 performs a rewards determination to determine if a reward is to be associated with the approved (or paid) adjudicated claim(s) received from the claim processor system 110. In an example embodiment of the invention, the rewards determination may include identifying the patient associated with the adjudicated claim, and if that patient qualifies for a reward to be associated with the adjudicated claim. A more detailed discussion of these determinations is described below with reference to FIGS. 3 and 4. In another embodiment of the invention, the rewards processing may occur outside of the prescription claim transaction processing activities. As an example, the transaction data may be delivered from the switch to an external rewards processing entity responsible for calculating the rewards, and the rewards calculations may occur off-line from the transaction processing system.

When it is determined that a reward is to be associated with the adjudicated prescription claim (e.g., a reward threshold was met or exceeded), a reward action may be performed. In example embodiments of the invention, a reward action may include inserting a message (or file) into the response delivered to the pharmacy system 104 and/or third party system, where the message (or file) includes a reward indicator 216 that indicates that the reward threshold has been exceeded and/or a reward may be applied to the transaction, as shown in FIG. 2. In other embodiments of the invention, other reward actions not shown in FIG. 2 may be performed. For instance, the reward action may include reducing an amount the patient is expected to pay. In another embodiment of the invention, the reward action may be to mail or email a reward notification message (e.g., coupon, voucher, reward points summary, etc.) to the patient when the patient has exceeded a reward threshold. In yet another embodiment of the invention, the reward action may include delivering a notification message (or file) to the corporate headquarters of the pharmacy to identify that the patient has exceeded a reward threshold. Once the pharmacy system 104 receives the reward indicator 216, the pharmacy may complete the filling of the prescription (if not already filled) and/or apply the reward that may be specified in the reward indicator 216.

In alternative embodiments of the invention, it is appreciated that one or more transmissions of a claim, adjudicated response, or reward indicator may bypass the switch (and/or the prescription rewards module 140, enrollment module 146, or claim processing module 144) when communicating with the intended entity (e.g., pharmacy, claim processor, or third party system). For example, in another embodiment of the invention, the pharmacy system 104 may create and transmit the claim 204 directly to the claim processor system 110.

The example process elements of FIG. 2 are shown by way of example, and other process and flow embodiments can have fewer or greater numbers of elements, and such elements can be arranged in alternative configurations in accordance with other embodiments of the invention.

Figure 3:
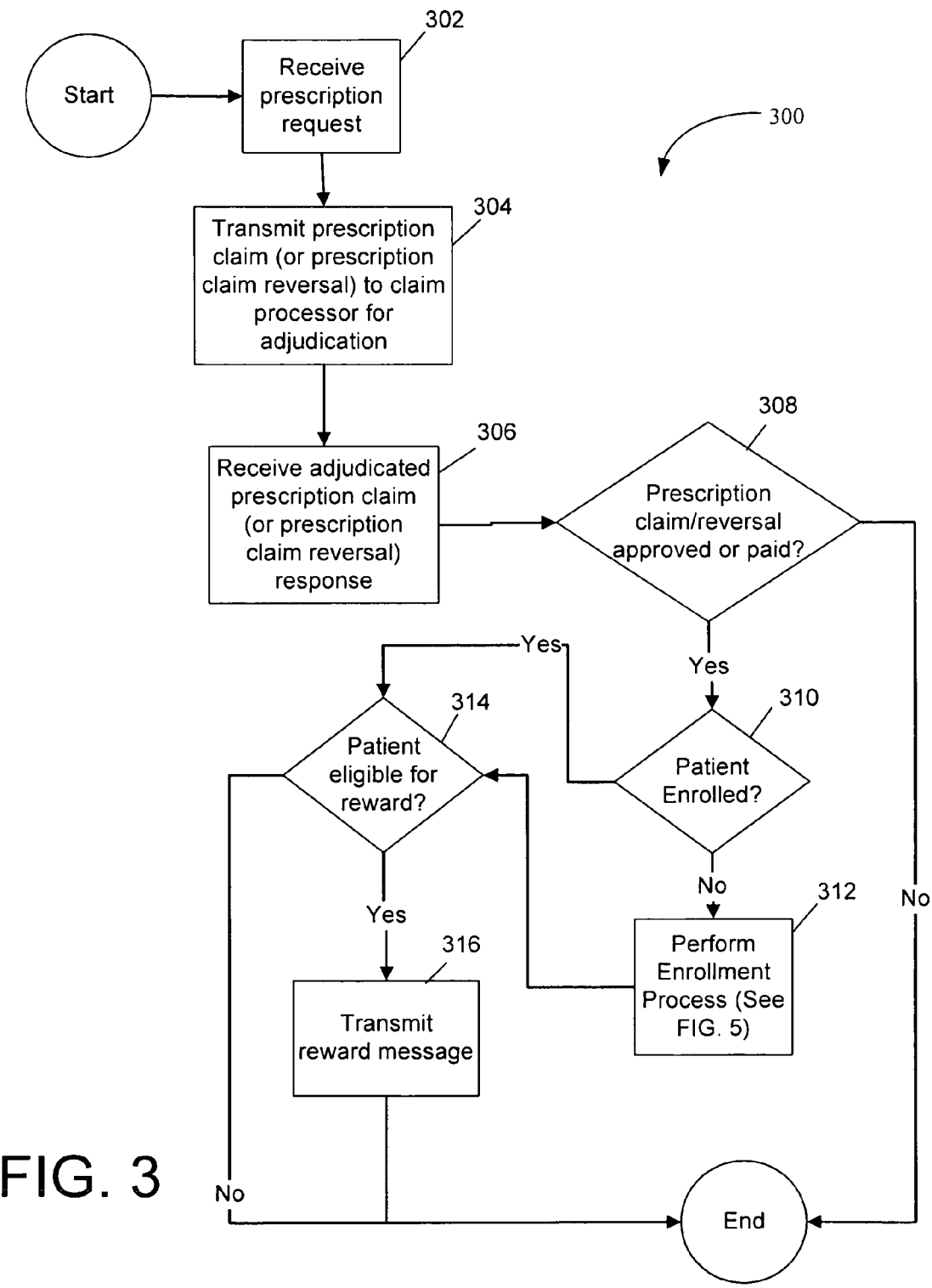
FIG. 3 shows an example flow diagram of processing prescription claim and/or prescription claim reversal transactions to manage prescription rewards in accordance with an example embodiment of the invention.

FIG. 3 shows an example flow diagram 300 of processing prescription claim and/or prescription claim reversal transactions to manage prescription rewards in accordance with an example embodiment of the invention. As shown in FIG. 3, the rewards processing begins with block 302 where a prescription to be fulfilled is provided to a pharmacy (e.g., new prescription, refill, partial fill, reversal, etc.). The prescription data to be included in the prescription transaction may include a patient first name, patient last name, patient street address, patient state/province code, patient ZIP/postal code, date of birth, and/or patient gender code. The prescription data may also include a pharmacy identifier, a physician identifier, an identifier for the medication or equipment (e.g., NDC), quantity dispensed, and the assigned days supply. In some embodiments of the invention, the prescription data may include a patient identifying number (e.g., a patient's Cardholder ID) if such an identifier previously exists, though such patient identifying number is not required for rewards processing.

In one example embodiment of the invention, the patient may present a prescription (i.e., paper form) to a pharmacist at the pharmacy. In an alternative embodiment of the invention, the prescription may be faxed to a particular pharmacy. In another alternative embodiment, the pharmacy may receive a prescription order request via a telephone call and/or captured via an Interactive Voice Response (IVR) system. In another alternative embodiment, the pharmacy may receive the prescription electronically from a transaction submitted from a healthcare provider's system to the pharmacy through the switch or otherwise. In example embodiments of the invention, the transaction standard for the electronic prescription submission may be one of National Council for Prescription Drug Programs (NCPDP) SCRIPT, American National Standards Institute (ANSI) X12, Health Level Seven (HL7), or similar transaction standards. Alternatively, the electronic transactions and/or the format of the transactions may be proprietary. The electronic prescription submission may specify the drug as well as include patient identification information, physician identification, BIN Number, group number, and any other information listed above as types of prescription data.

Once the pharmacy has received the prescription, block 304 is invoked where the pharmacy creates a claim for the filled, or to be filled, prescription (or claim reversal for a transaction to be reversed) to be submitted for adjudication to a claim processor (e.g., payer system) via the switch. Once the claim (or reversal) has been adjudicated by the claim processor, block 306 is invoked where an adjudicated response message is sent to, and received by, the switch. The adjudicated response message may indicate the results of the claim processor system's adjudication of the claim (or reversal) associated with the prescription. In an example embodiment of the invention, the submission of the claim (or reversal) may occur either before or simultaneously with filling the prescription for the prescribed drug.

Next, block 308 is invoked where the adjudicated claim is reviewed to determine if the adjudicated claim (or adjudicated claim reversal) response indicates that the prescription claim (or reversal) was approved or paid by the claim processor. If the adjudicated claim was not approved or paid by the claim processor, then the rewards processing may be aborted and a message may be sent to the pharmacy system indicating the adjudicated claim (or adjudicated claim reversal) as not being approved. If the adjudicated claim (or adjudicated claim reversal) was approved or paid by the claim processor, then step 310 may be invoked to determine if the patient associated with the approved claim has previously enrolled in a prescription rewards program. The determination as to whether or not the patient associated with the approved claim has previously enrolled in a prescription rewards program is described in further detail below with reference to FIGS. 4-5. If it is determined that the patient has not been previously enrolled in the prescription rewards program, then block 312 is invoked where the enrollment process described in FIG. 5 is performed. If it is determined that the patient has previously enrolled in the prescription rewards program, then block 314 is invoked to determine if the patient associated with the approved adjudicated claim (or approved adjudicated claim reversal) is eligible for a reward.

In an example embodiment of the invention, the patient's eligibility for a reward may be determined in a variety of ways including reviewing a patient database to determine if an entry may be found for the particular patient associated with the approved adjudicated claim (or approved adjudicated claim reversal). In an example embodiment of the invention, data cleansing and/or matching processes are applied to information submitted in a prescription claim (or reversal) transaction for adjudication and the technology cross-indexes all of the identified patients associated with a particular pharmacy (or pharmacy sponsor such as a chain, department store, grocery store, etc.). As an example, the system may determine that a Patient First Name of "Tom" is the abbreviated form of "Thomas" and the submission of "Tom" or "Thomas" may represent the same patient if all other matching criteria are met.

In an example embodiment of the invention, the pharmacy identifier, patient first name, patient last name, patient street address, patient state/province code, patient ZIP/Postal zone code, patient gender code, date of birth and/or any other identification information contained in the prescription claim (or reversal) request may be utilized in the data matching processes to match the patient with those included in a patient database or databases. In one example embodiment of the invention, the matching process may probabilistically match a patient with a database entry corresponding to that patient. For example, a match between the patient's first and last name contained in a prescription claim (or reversal) transaction and a name contained in a prescription rewards database for the patient may be given more weight than a match between the patient's street address or gender information, or three matches of certain types of identifying information may be considered a stronger match than five matches of other types of identifying information. In an example embodiment of the invention, adjustments to the match criteria and weight parameters associated with the various matching criteria may be made at the switch. As an another example, the system may determine that the first three positions of the submitted patient ZIP code probabilistically match a patient record containing matching criteria except the latter two positions of the patient ZIP code.

The database entry associated with a patient may indicate whether the patient is eligible for a reward. That database entry may be updated based on the approved adjudicated claim (or reversal). In an example embodiment of the invention, the database may track the number of approved adjudicated claims and/or claim reversals that the particular patient has been associated with within a predetermined time period (e.g., the past month, year, multiple years, etc.). Once the number of approved adjudicated claims reaches and/or exceeds a threshold (e.g., 10 approved prescription fills), then the patient may be eligible for a reward such as a co-pay discount, free prescription fill, voucher, or coupon for future use, or other type of reward or incentive. In another embodiment of the invention, the patient reward may be determined by the patient's out-of-pocket financial responsibility rather than the number of prescriptions. For example, when patients spend above a particular amount on prescriptions, then they receive a discount, voucher, or the like. In yet another embodiment of the invention, the system may reward points based on whether the prescription is filled, for instance, for a 30-day supply of the medication or a 90-day supply.

When the number of approved adjudicated claims reaches and/or exceeds the threshold, block 316 may be invoked where a reward indicator is created and communicated to the pharmacy system and/or third party system. In an example embodiment of the invention, the third party system may receive a reward indicator (e.g., message, report, file, etc.) containing an indication of the prescription fulfillment status through a web portal. In an alternative embodiment of the invention, the pharmacy system and/or a third party system such as a prescription rewards program sponsor may periodically request data relating to the rewards information and/or claim reversals associated with a particular patient or patients. The example process elements of FIG. 3 are shown by way of example, and other process and flow embodiments can have fewer or greater numbers of elements, and such elements can be arranged in alternative configurations in accordance with other embodiments of the invention. While FIG. 3 has described the general processing flow for prescription rewards processing, FIG. 4, discussed below, provides further details of specific embodiments of the invention.

Figure 4:
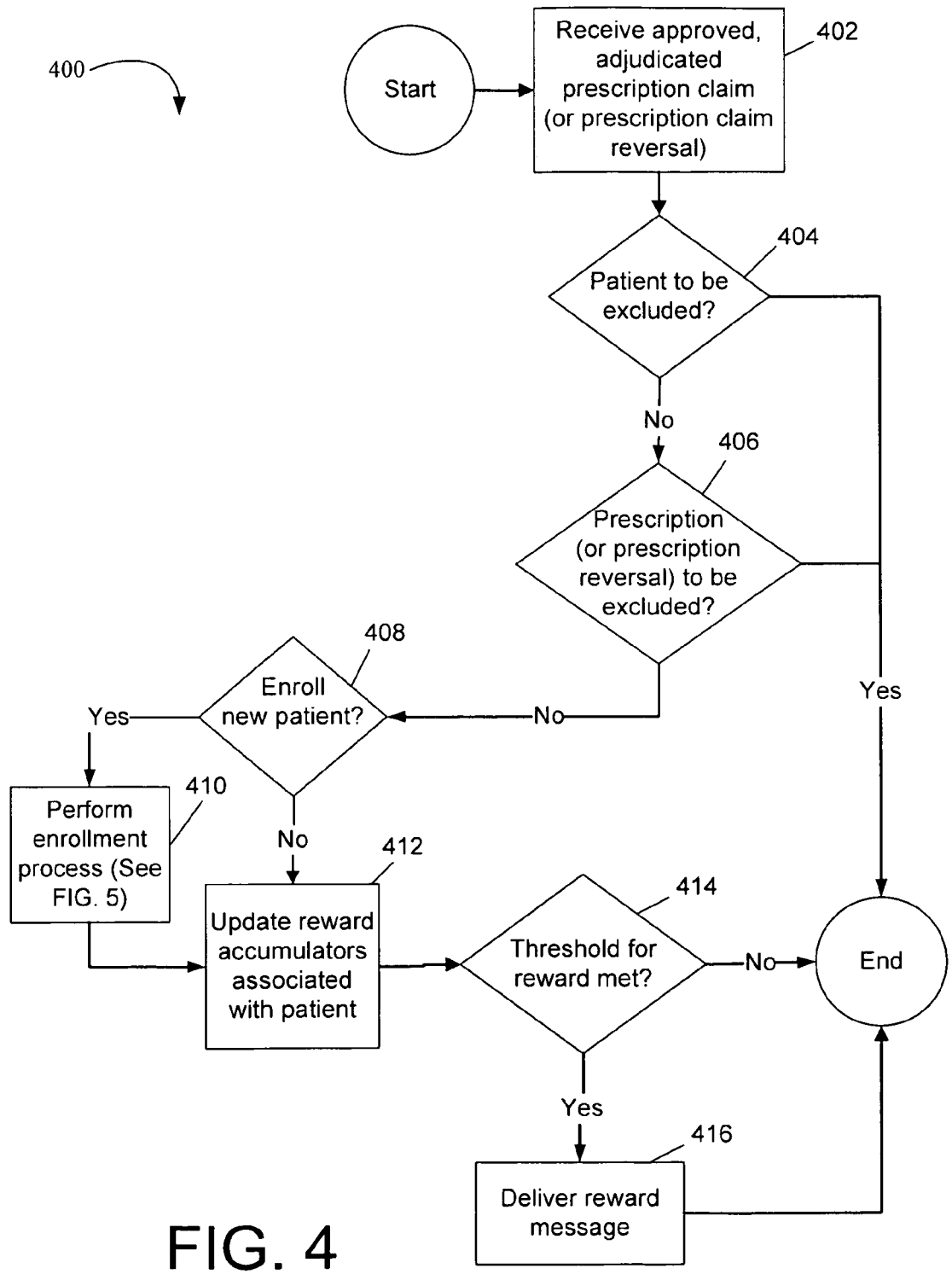
FIG. 4 shows an example flow diagram of one example embodiment of the rewards processing of approved prescription claim and/or approved prescription claim reversal transactions for managing prescription rewards in accordance with an example embodiment of the invention.
Figure 5:
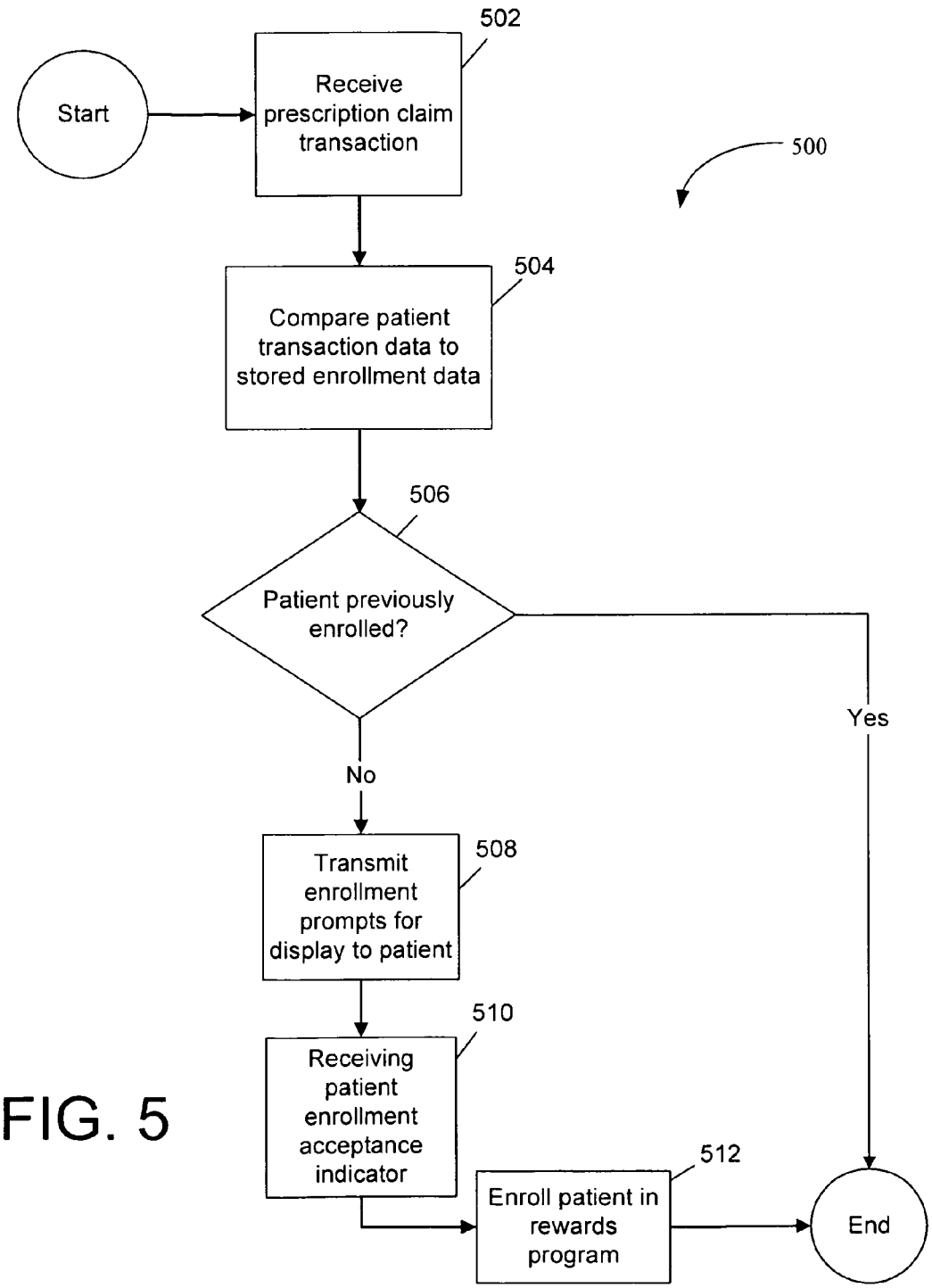
FIG. 5 shows an example flow diagram of one example embodiment of enrollment processing for patients enrolling in a prescription rewards program in accordance with an example embodiment of the invention.

FIG. 4 shows an example flow diagram 400 of one example embodiment of the rewards processing of approved prescription claim and/or approved prescription claim reversal transactions for managing prescription rewards in accordance with an example embodiment of the invention. As shown in FIG. 4, once the claim processor has returned an approved (or paid) prescription claim or claim reversal response (described above with reference to FIGS. 2 and 3), block 402 may be invoked where an adjudicated message pertaining to the approved prescription claim and/or approved prescription claim reversal is sent to, and received by, the switch. Next, block 404 is invoked to determine if a patient has requested to not be included in the rewards program and therefore should be excluded from the rewards processing. In an example embodiment of the invention, an indicator of the patient's exclusion from the rewards program may be stored in a database entry for the patient such as in the EMPI. An indication of exclusion of rewards consideration of a particular patient may be provided to the switch for inclusion in the database from the pharmacy system with the prescription transaction (e.g., at the request of the patient) or through a file containing a listing of patients to be excluded for future prescription transactions provided by the pharmacy or the reward sponsor entity (e.g., pharmacy chain, department store, grocery store, or other rewards program sponsor entity). Such a file listing those patients to be excluded from rewards processing may be updated on a periodic basis (e.g., monthly, weekly, daily) or as necessary. In an example embodiment of the invention, the adjudicated prescription claim may be compared against the indication of patient exclusion in the stored listing of that information. If the patient associated with the adjudicated claim is to be excluded from rewards processing, then the rewards processing is aborted. If the patient associated with the adjudicated claim is not excluded from the rewards processing, then the process continues to block 406.

Block 406 determines if the adjudicated prescription claim should be excluded from rewards consideration. In one example embodiment of the invention, a prescription claim that was adjudicated by a government sponsored healthcare program (e.g., Medicare, Medicaid, or the like) may be excluded from rewards processing. In an example embodiment of the invention, many government sponsored healthcare programs may need to be excluded from rewards consideration due to legal restrictions on the application of rewards (e.g., discounts, vouchers related to co-pays, reimbursements, etc.) to prescription transactions that are adjudicated by government sponsored healthcare programs. In an example embodiment of the invention, a list of government sponsored healthcare programs for funding prescriptions may be maintained at the switch and/or maintained in a database accessible by the switch where the adjudicated claim transaction may be compared against the list to determine if that transaction should be excluded from rewards processing. In an alternative embodiment of the invention, the pharmacy practice management system may communicate an indicator in the prescription claim request or prescription claim reversal request to indicate the patient should be excluded from participation in the rewards program.

In alternative embodiments of the invention, other reasons may also be established to exclude certain prescription claim and/or claim reversal transactions from rewards processing including factors such as the jurisdiction a particular pharmacy is in, quantity of the drug(s) to be dispensed, partial fill transactions, days supply, reimbursement financial considerations, or other factors that may be established by the pharmacy, pharmacy sponsor, or other entity. If it is determined that the adjudicated prescription claim (or reversal) is to be excluded (e.g., the adjudicated prescription claim is associated with a government sponsored healthcare program) then the rewards processing for that prescription claim is aborted. If it is determined that the adjudicated prescription claim (or reversal) is not to be excluded, then the rewards processing continues to block 408.

When block 408 is invoked a determination is made as to whether or not the patient associated with the adjudicated prescription claim (or reversal) has previously enrolled in the prescription rewards program and is therefore already included in a patient database (e.g., the patient had previously submitted a prescription transaction to a pharmacy system participating in the rewards program and enrolled in the rewards program). In an example embodiment of the invention, the determination may be made through a matching process applied to potential patient identifying data including the pharmacy, patient, physician, and claim information contained in the prescription claim (or reversal) transaction to determine if there is a match between the patient associated with the prescription claim (or reversal) transaction submitted for adjudication and patient identification information indexed by the database (e.g., EMPI). In an example embodiment of the invention, the matching process weighs the strength of the matched patient identifying data contained in the prescription claim (or reversal) transaction and the patient identification data maintained in a prescription rewards database to determine if the patient associated with the submitted claim (or reversal) transaction corresponds to a patient entry in the prescription rewards database. In one alternative embodiment of the invention, the patient identifying data may include a pre-existing patent identifying number (e.g., credit card number, bar code, etc.) and the patient identifying numbers may be utilized in the matching process described above. However, such patient identifying numbers may not be required for the matching process to match the patient associated with the prescription claim (or reversal) transaction with a corresponding database entry.

In example embodiments of the invention, the EMPI may be used to identify whether or not a patient is enrolled in a prescription rewards program (or member patient's family, for instance, under the same healthcare insurance plan) using probabilistic matching techniques typically based on demographic information associated with the patient of the submitted transaction. For example, a transaction containing a patient's telephone number, date of birth, and zip code, may be used to determine that the patient associated with the submitted transaction is enrolled in a prescriptions rewards program and his or her associated reward information should be updated and/or applied accordingly.

If it is determined that the patient associated with the adjudicated claim (or reversal) response is located in the patient database (e.g., EMPI), then a new patient database entry is not necessary, and the rewards processing proceeds to block 412. If it is determined that the patient associated with the adjudicated claim (or reversal) response is not located in the patient database, block 410 is invoked where the enrollment process described below with reference to FIG. 5, including creating a new patient database entry, is performed and the process then continues to block 412.

In block 412, the patient database entry for the patient associated with the adjudicated prescription claim (or reversal) is updated to indicate the approved prescription claim (or reversal) transaction. In the example embodiment of the invention described in FIG. 4, the database may track the number of approved adjudicated claims and/or reversals that the particular patient has been associated with within a predetermined time period (e.g., the past month, year, multiple years, etc.). In an example embodiment of the invention, when an approved adjudicated prescription claim transaction is for a prescription fill (or refill) an accumulator associated with the patient's database record in the database (e.g., EMPI) may be incremented. However, if the approved adjudicated prescription claim transaction is for a prescription claim reversal, then the accumulator associated with the patient's database record in the database (e.g., EMPI) is decremented. While an example embodiment of the invention may provide a single increment for each prescription claim transaction, in alternative embodiments of the invention various incremental values may be associated with various aspects of the transactions. For example, the date of the transaction may indicate incrementing the accumulator multiple times for each prescription fill occurring on that date, or incrementing the accumulator multiple values if the prescription is directed to a particular drug, or a particular pill count. Therefore, in example embodiments of the invention other transaction parameters or patient identification information may be used to alter the rewards processing associated with a customer's pharmacy use thereby varying the frequency or amount of rewards, incentives, discounts or the like provided to customers.

In one example embodiment of the invention, the patient's accumulator value may be updated in a real time format as adjudicated claims and/or reversals are received. In an alternative embodiment of the invention, the patient's accumulator value may be updated in a batch format considering multiple prescription claims associated with a particular patient over a time period. The transactions may include claims for both prescription fills and reversals, which are all processed to produce a new accumulator value to be associated with the patient's record in the database (e.g., EMPI). For example, in the batch processing embodiment, a patient may have had three prescriptions filled and one prescription reversal transaction. In an example embodiment of the invention, to determine the appropriate accumulator value, the reversal transaction may be reviewed against the prescription fill transactions to determine if the reversal is associated with one or more of the prescription fill transactions and should therefore cancel out the corresponding transaction(s). In an example embodiment of the invention, the reversal transaction must share the same provider ID, prescription number, and date of service as the prescription fill transaction to cancel out the corresponding prescription fill transaction(s) for accumulation purposes. Therefore, when claims for two prescription fill transactions and one prescription reversal transaction have been adjudicated, and when the prescription reversal transaction matches one of the prescription fill transactions, then the accumulator will cancel those two transactions and only consider the remaining prescription fill transaction for accumulation.

Next, block 414 is invoked where a determination of whether the number of approved adjudicated claims reflected in the accumulator reached and/or exceeded a threshold (e.g., 10 approved prescription fills) with the most recent approved adjudicated prescription claim. If the threshold has been reached, then the patient may be eligible for a reward such as a co-pay discount, free prescription fill, voucher, or coupon for future use, or other type of reward or incentive. If the threshold has not been reached and/or exceeded, then the rewards processing has ended. If the number of approved adjudicated claims has reached and/or exceeded the threshold, block 416 may be invoked where a reward indicator is created and communicated to the pharmacy system and/or third party system. In an example embodiment of the invention, a third party system, pharmacy system, and/or the patient may receive a reward indicator (e.g., message, report, file, etc.) containing an indication of the prescription fulfillment status through a web portal. Reporting rewards processing information to the pharmacy or third party systems such as a rewards sponsor entity may include identifying new patients or unique patients, identifying patients reaching and/or exceeding accumulator thresholds, or identifying patient based exclusions or transaction based exclusions (e.g., government funded transactions). In an example embodiment of the invention, the frequency of the reporting may be on a periodic basis (e.g., monthly, weekly, daily, etc.), or alternatively the report may be generated automatically or on demand. In an example embodiment of the invention, the report may be transmitted to the pharmacy and/or third party as an electronic file, fax, email, or the like, or accessible via a web portal through a secure log-in. The example process elements of FIG. 4 are shown by way of example, and other process and flow embodiments can have fewer or greater numbers of elements, and such elements can be arranged in alternative configurations in accordance with other embodiments of the invention.

FIG. 5 shows an example flow diagram 500 of one example embodiment of enrollment processing for patients enrolling in a prescription rewards program in accordance with an example embodiment of the invention. As shown in FIG. 5, the prescription rewards program enrollment process begins at block 502 where a prescription claim transaction is received at the switch and patient identification data (e.g., patient's last name, date of birth, zip code, etc.) contained in the prescription claim transaction is provided to the enrollment module. Next, block 504 is invoked where the patient identification data is compared to previously stored enrollment data in a database to determine if the provided patient identification data matches any enrollment data in the database. Block 506 is then invoked to determine if the comparison resulted in any matches that indicate that the patient associated with the submitted prescription claim transaction has previously enrolled in the prescription rewards program. The matching process may use some or all of the patient identification data to determine a match.

In one example embodiment of the invention, the match may be performed at a family level and not the individual patient level. In such an embodiment, matching may be performed only information that would be applicable to the patient's family (e.g., those sharing the same healthcare coverage plan) such as the patient's last name, home street address, zip code, etc. Other embodiments may require patient level matching based on patient specific information (e.g., date of birth, etc.). In some embodiments of the invention, the matching process does not require exact matches, but rather probabilistic matches based on one or more matching criteria, or sophisticated algorithms (e.g., algorithms that do not require exact spelling of a name to make a potential match, etc.).

In example embodiments of the invention, the EMPI may be used to identify whether or not a patient is enrolled in a prescription rewards program (or member patient's family, for instance, under the same healthcare insurance plan) using probabilistic matching techniques typically based on demographic information associated with the patient of the submitted transaction. For example, a transaction containing a patient's telephone number, date of birth, and zip code may be used to determine that the patient associated with the submitted transaction is enrolled in a prescription rewards program and the patient's associated reward information should be updated and/or applied accordingly.

If a match was found and indicates that the patient has previously enrolled in the prescription rewards program, then the enrollment process is exited. If a match is not found, then block 508 may be invoked where an enrollment message may be sent to the pharmacy POS device for the patient to review and to prompt the patient to agree to enrolling in the prescription rewards program. In an example embodiment of the invention, the format of the enrollment message may be that of a denied claim response, where the denied claim response prompts the patient to enter an enrollment indicator (e.g., a numerical code, etc.) When the patient agrees to enroll in the prescription rewards program, the pharmacy resubmits the prescription claim request with a patient enrollment indicator, and the resubmission of the prescription claim request is received by the enrollment module in block 510. Next, block 512 is invoked where the database storing enrollment data is updated to reflect that the patient is now enrolled in the prescription rewards program.

The example process elements of FIG. 5 are shown by way of example, and other process and flow embodiments can have fewer or greater numbers of elements, and such elements can be arranged in alternative configurations in accordance with other embodiments of the invention.

Accordingly, many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of this application. Although specific terms are employed herein, they are used in a generic and descriptive sense only and not for purposes of limitation.

The invention claimed is:

1. A computer-implemented method, comprising:
receiving, at a switch comprising one or more computers, a prescription claim transaction from a pharmacy computer associated with a pharmacy, the prescription claim transaction comprising patient identification data for a patient and an identifier for a medication being requested by the patient;
retrieving, with the switch, the patient identification data from the prescription claim transaction;
automatically enrolling, with the switch, the patient identified by the patient identification data in the prescription claim transaction in a prescription rewards program using at least a portion of the retrieved patient identification data, wherein the enrollment includes the switch associating the patient identification data used in the automatic enrollment with a reward accumulator value;
transmitting, by the switch, the prescription claim transaction from the switch to a claims processor computer associated with a claims processor for adjudication;
receiving, at the switch, the adjudicated prescription claim transaction from the claims processor computer, wherein the adjudicated prescription claim transaction includes an indication that the prescription claim transaction has been approved by a claim processor;
identifying, at the switch from the adjudicated prescription claim transaction, a patient associated with the adjudicated prescription claim transaction;
retrieving, by the switch from a database associated with the switch, the reward accumulator value associated with the patient; and
updating, at the switch, the reward accumulator value associated with the patient based at least in part on the adjudicated prescription claim transaction, the reward accumulator value being incremented based upon the indication that the prescription claim transaction has been approved.

2. The computer-implemented method of claim 1, further comprising:
determining, by the switch, that a threshold value has been satisfied by the reward accumulator value; and
issuing, by the switch, a reward message based at least in part on the reward accumulator satisfying the threshold value.

3. The computer-implemented method of claim 2, wherein issuing a reward message comprises issuing a reward message that indicates a discount associated with the payment of a prescription.

4. The computer-implemented method of claim 1, further comprising:
determining, by the switch, that the prescription associated with the prescription claim transaction is eligible for rewards processing prior to retrieving a reward accumulator value associated with the patient.

5. A system comprising:
a memory device, wherein the memory device stores a plurality of reward accumulator values, wherein each reward accumulator value is associated with a patient; and
a switch processor in communication with the memory device, wherein the switch processor is configured to execute computer-executable instructions to:

receive a prescription claim transaction from a pharmacy computer associated with a pharmacy, the prescription claim transaction comprising patient identification data for a patient and an identifier for a medication being requested by the patient,
retrieve the patient identification data from the prescription claim transaction,
automatically enroll the patient identified by the patient information in the prescription claim transaction in a prescription rewards program using at least a portion of the retrieved patient identification data, wherein the enrollment includes associating the patient identification data used in the automatic enrollment with one of the plurality of reward accumulator values,
direct communication of the prescription claim transaction to a claims processor computer associated with a claims process for adjudication of the prescription claim transaction;
receive the adjudicated prescription claim transaction from the claims processor computer, wherein the adjudicated prescription claim transaction includes an indication that the prescription claim transaction has been approved by a claim processor,
identify, from the adjudicated prescription claim transaction, a patient associated with the adjudicated prescription claim transaction,
retrieve, from the memory device, a reward accumulator value associated with the patient, and
update the reward accumulator value associated with the patient based at least in part on the adjudicated prescription claim transaction, the reward accumulator value being incremented based upon the indication that the prescription claim transaction has been approved,
wherein the switch processor is associated with a switch that routes prescription claim transactions between one or more pharmacy systems and one or more claims processor systems.

6. The system of claim 5, wherein the switch processor is further configured to execute instructions to:
determine that a threshold value has been satisfied by the reward accumulator value, and
issue a reward message based at least in part on the reward accumulator value satisfying the threshold value.

7. The system of claim 6, wherein the computer-executable instructions to issue a reward message include issuing a reward message that indicates a discount associated with the payment of a prescription.

8. The system of claim 5, wherein the switch processor is further configured to execute instructions to:
determine that the prescription associated with the prescription claim transaction is eligible for rewards processing prior to retrieving a reward accumulator value associated with the patient.

9. The computer-implemented method of claim 1, wherein the reward accumulator value is associated with a rewards program, wherein the rewards program does not utilize a rewards card having a particular rewards identifier for the patient.

10. The system of claim 5, wherein the reward accumulator value is associated with a rewards program, wherein the rewards program does not utilize a rewards card having a particular rewards identifier for the patient.

11. The computer-implemented method of claim 2, wherein determining that a threshold value has been satisfied by the reward accumulator value comprises:

determining, by the switch, a patient co-pay amount from at least the adjudicated prescription claim transaction, wherein the reward accumulator value comprises the patient co-pay amount;

comparing, by the switch, the patient co-pay amount to the threshold value to determine if the patient co-pay amount exceeds the threshold value; and determining, by the switch, that the threshold value has been satisfied by the reward accumulator value based on a positive determination that the patient co-pay amount exceeds the threshold value.

12. The computer-implemented method of claim 2, wherein the reward message comprises a reduction in a patient co-pay amount in the current adjudicated prescription claim transaction.

13. The computer-implemented method of claim 2, wherein issuing, by the switch, the reward message comprises the switch emailing the reward message directly to the patient.

14. The computer-implemented method of claim 1, wherein updating the reward accumulator value, the reward accumulator value being incremented based upon the indication that the prescription claim transaction has been approved, further comprises:

identifying, by the switch, the identifier for the medication requested by the patient in the adjudicated prescription claim transaction;

determining, by the switch, that the identified medication is one for which the reward accumulator value is incremented a plurality of times; and incrementing, by the switch, the reward accumulator value the plurality of times based on the identified medication in the adjudicated prescription claim transaction.

15. The system of claim 6, wherein the switch processor is further configured to determine that a threshold value has been satisfied by the reward accumulator value by executing instructions to:

determine a patient co-pay amount from at least the adjudicated prescription claim transaction, wherein the reward accumulator value comprises the patient co-pay amount;

compare the patient co-pay amount to the threshold value to determine if the patient co-pay amount exceeds the threshold value; and determine that the threshold value has been satisfied by the reward accumulator value based on a positive determination that the patient co-pay amount exceeds the threshold value.

16. The system of claim 6, wherein the reward message comprises a reduction in a patient co-pay amount in the current adjudicated prescription claim transaction.

17. The system of claim 6, wherein the switch processor is further configured to issue the reward message by executing instructions to direct communication of the reward message directly to the patient by electronic mail.

18. The system of claim 5, wherein the switch processor is configured to update the reward accumulator value, the reward accumulator value being incremented based upon the indication that the prescription claim transaction has been approved, by executing instructions to:

identify the identifier for the medication requested by the patient in the adjudicated prescription claim transaction;

determine that the identified medication is one for which the reward accumulator value is incremented a plurality of times; and increment the reward accumulator value the plurality of times based on the identified medication in the adjudicated prescription claim transaction.

* * * * *